United States Patent
Wakamatsu et al.

Patent Number: 5,237,059
Date of Patent: Aug. 17, 1993

[54] COMPOUNDS CAPABLE OF GENERATING AN ACID BY LIGHT IRRADIATION

[75] Inventors: Kan Wakamatsu; Yuichi Wakata, both of Shizuoka, Japan

[73] Assignee: Fuji Photo Film Co., Ltd., Tokyo, Japan

[21] Appl. No.: 854,853

[22] Filed: Mar. 20, 1992

[30] Foreign Application Priority Data

Mar. 22, 1991 [JP] Japan .................. 3-059025

[51] Int. Cl.⁵ .................. C07D 205/10; C07C 309/74
[52] U.S. Cl. .................. 540/355; 546/204; 546/285; 548/451; 548/474; 548/528; 552/221; 552/234; 558/301
[58] Field of Search .............. 548/474, 451, 528; 546/204, 285; 540/355; 552/221, 234; 558/301

[56] References Cited

U.S. PATENT DOCUMENTS 4,618,564 10/1986 Demmer et al. .................. 430/270

FOREIGN PATENT DOCUMENTS 0199672 6/1988 European Pat. Off. .
64-18143 1/1989 Japan .

Primary Examiner—Joseph Paul Brust
Assistant Examiner—Jacqueline Haley
Attorney, Agent, or Firm—Sughrue, Mion, Zinn, Macpeak & Seas

[57] ABSTRACT

A compound capable of generating an acid by light irradiation selected from the group consisting of oxime sulfonic acid esters of formula (I):

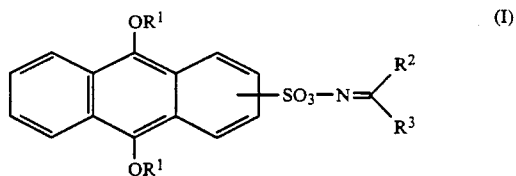

wherein $R^1$ is an alkyl group, each of $R^2$ and $R^3$ is selected from the group consisting of a hydrogen atom, a substituted or unsubstituted alkyl group, a substituted or unsubstituted aryl group and a cyano group, and $R^2$ and $R^3$ may optionally combine to form a ring; and N-hydroxyimidesulfonic acid esters of formula (II):

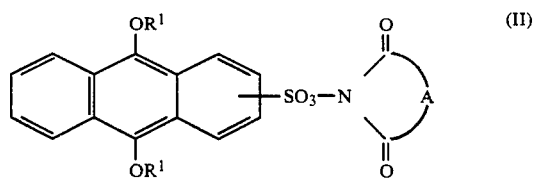

wherein $R^1$ is an alkyl group, and A is a group selected from the group consisting of a substituted or unsubstituted arylene group, a substituted or unsubstituted alkylene group and a substituted or unsubstituted alkenylene group, wherein the compound capable of generating an acid by light irradiation is useful as an image-forming materials, etc. and has high reactivity to light of from the near ultraviolet region to the visible region.

3 Claims, No Drawings

COMPOUNDS CAPABLE OF GENERATING AN ACID BY LIGHT IRRADIATION

FIELD OF THE INVENTION

This invention relates to novel compounds capable of generating an acid by light irradiation, which are useful as image-forming materials, etc.

BACKGROUND OF THE INVENTION

Compounds generating an acid by light irradiation are useful for cationic polymerization with an acid as a catalyst, and image-forming materials utilizing, for example, coloration and discoloration of dyes with acids.

Compounds of this type heretofore known include Lewis acid-generating compounds typified by aryl diazonium salts described in S. I. Schlesinger, *Photographic Science and Technology*, Vol. 18, page 387 (1974), etc.; onium salts typified by diaryl iodonium salts described in J. V. Crivello et al., *Macromolecules*, Vol. 10, page 1307 (1977), etc.; oxime sulfonic acid esters described in European Patent 199672, etc.; N-hydroxyimidesulfonic acid esters described in U.S. Pat. No. 4,618,564, etc.; and Bronsted acid-generating compounds such as nitrobenzylsulfonic acid esters described in *Macromolecules*, Vol. 21, page 2001 (1988), etc.

However, many of these compounds are sensitive only to ultraviolet light, and their sensitivity to light of from the near ultraviolet region to the visible region (i.e., the wavelength region longer than the 300–350 nm region, more specifically, the wavelength region of from about 350 nm to about 600 nm), such as light of an argon laser, is low.

The 9,10-dialkoxyanthracenesulfonic acid 4-nitrobenzyl esters described in JP-A-64-18143 (the term "JP-A" as used herein and hereinafter means an "unexamined published Japanese patent application") are known to be sensitive to light of from the near ultraviolet region to the visible region. However, the compounds disclosed in JP-A-64-18143 have a low reactivity and compounds having a higher reactivity are not known in the art.

SUMMARY OF THE INVENTION

An object of this invention is to provide novel compounds capable of generating an acid by light irradiation which are useful as image-forming materials and which have a high reactivity to light of from the near ultraviolet region to the visible region.

The above-stated problems have been solved through the development of a compound capable of generating an acid by light irradiation selected from the group consisting of oxime sulfonic acid esters of formula (I):

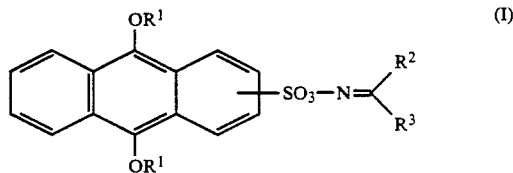

wherein $R^1$ is an alkyl group, each of $R^2$ and $R^3$ is selected from the group consisting of a hydrogen atom, a substituted or unsubstituted alkyl group, a substituted or unsubstituted aryl group and a cyano group, and $R^2$ and $R^3$ may optionally combine to form a ring; and N-hydroxyimidesulfonic acid esters of formula (II):

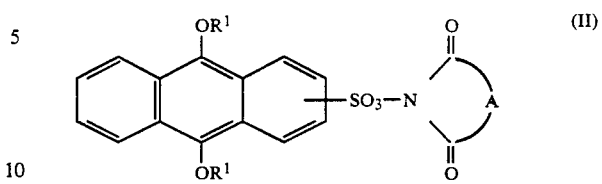

wherein $R^1$ is an alkyl group, and A is a group selected from the group consisting of a substituted or unsubstituted arylene group, a substituted or unsubstituted alkylene group, and a substituted or unsubstituted alkenylene group.

DETAILED DESCRIPTION OF THE INVENTION

In the compound of formula (I) and formula (II), $R^1$ is an alkyl group, preferably a $C_{1-8}$ alkyl group, and more preferably a $C_{1-4}$ alkyl group.

Illustrative examples of $R^1$ include, for instance, methyl, ethyl, n-propyl, i-propyl, n-butyl, i-butyl, sec-butyl, t-butyl, pentyl, hexyl, heptyl, octyl, 2-ethylhexyl.

In the compound of formula (I), $R^2$ and $R^3$, which may be the same or different, each is a hydrogen atom, a substituted or unsubstituted alkyl group, a substituted or unsubstituted aryl group or a cyano group, and $R^2$ and $R^3$ may optionally combine to form a ring. Preferably, each of $R^2$ and $R^3$ is a hydrogen atom, a substituted or unsubstituted $C_{1-8}$ alkyl group, a substituted or unsubstituted $C_{6-10}$ aryl group or a cyano group, and $R^2$ and $R^3$ may optionally combine to form a ring having 4 to 14 carbon atoms. Each of the substituents on the alkyl and aryl groups in the meaning of $R^2$ and $R^3$ is preferably halogeno, $C_{1-6}$ alkyl, $C_{6-10}$ aryl, $C_{1-8}$ ester, amido, $C_{1-8}$ alkoxy, or nitro. More preferably, each of $R^2$ and $R^3$ is a hydrogen atom, a $C_{1-6}$ alkyl group, a halogenated $C_{1-6}$ alkyl group, a $C_{6-10}$ aryl group or a cyano group, and $R^2$ and $R^3$ may optionally combine to form a ring having 4 to 14 carbon atoms.

Illustrative examples of $R^2$ and $R^3$ in formula (I) include, for instance, a hydrogen atom, methyl, ethyl, n-propyl, i-propyl, n-butyl, i-butyl, sec-butyl, t-butyl, pentyl, hexyl, heptyl, octyl, 2-ethylhexyl, trifluoromethyl, chloromethyl, bromomethyl, 2-methoxycarbonylethyl, phenylethyl, phenyl, naphthyl, methoxyphenyl, methylphenyl, ethoxycarbonylphenyl, aminocarbonylphenyl, nitrophenyl and cyano, and examples of the ring which $R^2$ and $R^3$ may combine to form include, for instance, a fluorene ring, a tetrahydronaphthyl ring, a cyclohexane ring, a cyclohexene ring, and a cyclopentane ring.

In the compound of formula (II), A is a substituted or unsubstituted arylene group, a substituted or unsubstituted alkylene group, or a substituted or unsubstituted alkenylene group.

Preferably, A is a substituted or unsubstituted $C_{6-10}$ arylene group, a substituted or unsubstituted $C_{2-10}$ alkylene group, or a substituted or unsubstituted $C_{2-10}$ alkenylene group. Each of the substituents on the arylene, alkylene and alkenylene groups in the meaning of A is preferably halogeno, $C_{1-6}$ alkyl, $C_{6-10}$ aryl, $C_{1-8}$ ester, amido, $C_{1-8}$ alkoxy, or nitro. More preferably, A is a $C_{6-10}$ arylene group, a $C_{2-6}$ alkylene group, or a $C_{2-6}$ alkenylene group.

Illustrative examples of A in formula (II) include, for instance, phenylene, naphthylene, nitrophenylene, bromophenylene, tetrabromophenylene, chlorophenylene, tatrachlorophenylene, nitronaphthylene, ethylene, cyclohexylene, vinylene, cyclohexenylene, phenylethylene, phenylvinylene, methylvinylene, methoxyphenylene, ethoxycarbonylphenylene, and aminocarbonylphenylene.

The compounds of formula (I) are obtained by condensing a sulfonyl chloride of formula (III):

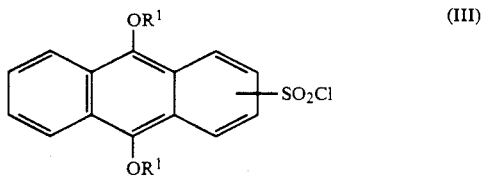

wherein $R^1$ is as defined above and an oxime of formula (IV):

wherein $R^2$ and $R^3$ are as defined above, in the presence of a deacidifying agent. Likewise, the compounds of formula (II) can be obtained by condensing the sulfonyl chloride of the above formula (III) and an N-hydroxyimide of formula (V):

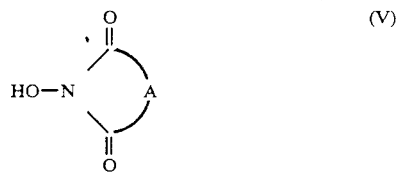

wherein A is as defined above, in the presence of a deacidifying agent.

The sulfonyl chloride represented by formula (III) can be synthesized by the method described in, for example, JP-A-64-18143.

Illustrative examples of the sulfonyl chlorides of formula (III) include, for instance, 9,10-dimethoxyanthracene-2-sulfonyl chloride, 9,10-diethoxyanthracene-2-sulfonyl chloride, 9,10-di-n-propylanthracene-2-sulfonyl chloride, 9,10-di-i-propylanthracene-2-sulfonyl chloride, 9,10-di-n-butylanthracene-2-sulfonyl chloride, 9,10-di-i-butylanthracene-2-sulfonyl chloride, 9,10-di-sec-butylanthracene-2-sulfonyl chloride, 9,10-di-t-butylanthracene-2-sulfonyl chloride, 9,10-dipentyloxyanthracene-2-sulfonyl chloride, 9,10-diheptyloxyanthracene-2-sulfonyl chloride, 9,10-dioctyloxyanthracene-2-sulfonyl chloride, 9,10-di(2-ethylhexyloxy) anthracene-2-sulfonyl chloride.

Illustrative example of oximes of formula (IV) include, for instance, 2-hydroxyimino-2-phenylacetonitrile, 1-hydroxyiminoethane, 2-hydroxyiminopropane, 2hydroxyiminobutane, 4-phenyl-2-hydroxyiminobutane, cyclohexanone oxime, cyclohexenone oxime, cyclopentanone oxime, 1,1,1-trifluoroacetophenone oxime, acetonaphthone oxime, 1-hydroxyimino-1,2,3,4-tetrahydronaphthalene benzophenoneoxime oxime, 4'-chlorobenzophenone oxime, 4'-methylacetophenone oxime, 4'-methoxyacetophenone oxime, 4'-methoxycarbonylacetophenone oxime, 4'-aminocarbonyl acetophenone oxime, 4'-nitroacetophenone oxime, 9fluorenoneoxime.

Illustrative examples of N-hydroxyimides of formula (V) include, for example, N-hydroxyphthalimide, 4-methyl-N-hydroxyphthalimide, 3-nitro-N-hydroxyphthalimide, 4-nitro-N-hydroxyphthalimide, 4-methoxy-N-hydroxyphthalimide, 4-methoxycarbonyl-N-hydroxyphthalimide, 4-aminocarbonyl-N-hydroxyphthalimide, 4-bromo-N-hydroxyphthalimide, 4-chloro-N-hydroxyphthalimide, 3,4,5,6-tetrachlorophthalimide, 3,4,5,6tetrabromophthalimide, N-hydroxysuccinimide, N-hydroxycyclohexanimide, N-hydroxycyclohexenimide, N-hydroxy-1,8-naphthalimide, 3-nitro-N-hydroxy-1,8-naphthalimide, N-hydroxymaleinimide, N-hydroxyphenylmaleinimide, N-hydroxycitraconimide, N-hydroxyglutarimide.

Various organic solvents may be used as reaction solvents. Of these, diethyl ether, acetone, dichloromethane, chloroform, carbon tetrachloride, tetrahydrofuran, dioxane, benzene, toluene and acetonitrile are preferred. Examples of the deacidifying agents are various organic amines, and of these, pyridine, diethylamine, triethylamine, N,N-dimethylaniline and N,N-diethylaniline are preferably used.

Preferably, the reaction is carried out by using 1 to 1.2 equivalents of the compound of formula (V) and 1 to 1.2 equivalents of the deacidifying agent per mole equivalent of the compound of formula (III). The reaction temperature is preferably −10 to 40° C.

The compounds of the present invention have a high reactivity to light of from the near ultraviolet region to the visible region, and are capable of generating an acid imagewise by, for example, a scanning exposure using an argon ion laser.

Accordingly, the compounds of the present invention are useful for cationic polymerization with an acid as catalyst, and image-forming materials utilizing coloration and discoloration of dyes, such as a photoresist for a printed wiring board, a printed board, a photoresist for an LSI, a print-proofing material, and an image-displaying material, etc.

Examples of the present invention are given below by way of illustration but are not to be construed as limiting the present invention. Unless otherwise indicated herein, all parts, percents, ratios and the like are by weight.

EXAMPLE 1

Synthesis and Evaluation of
2-(9,10-Dibutoxyanthracene-2-sulfonyloxy)
imino-2-phenylacetonitrile A mixture of 0.50 g of 2-hydroxyimino-2-phenylacetonitrile, 1.43 g of 9,10-dibutoxyanthracene-2-sulfonyl chloride and 20 ml of dichloromethane was stirred on an ice bath, and 0.34 g of triethylamine was added.

The mixture was stirred at room temperature (about 20°-30° C.), and after confirming that the starting materials had dissolved using thin-layer chromatography, the product was washed with water, dried, and the solvent was distilled off to obtain a yellow oily product. The product was purified by column chromatography to obtain 0.56 g of the desired compound in the form of a yellow oily product.

This compound was dissolved in methyl ethyl ketone, and light irradiation was applied to the solution for 10 seconds by using a superhigh pressure mercury lamp. Then, a leuco dye, an acid-coloring agent having formula (VI):

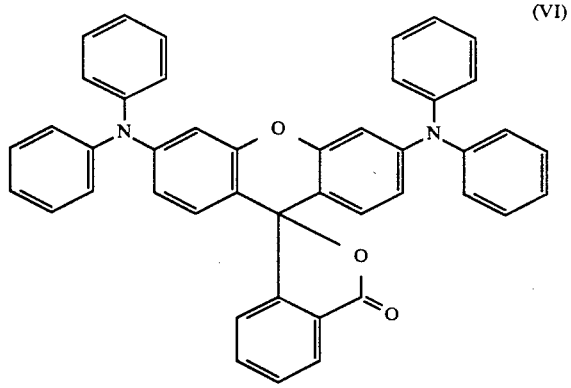

(VI)

was added, whereby the product became a brilliant blue color and the generation of an acid was observed.

EXAMPLE 2

Synthesis and Evaluation of 2-(9,10-Dimethoxyanthracene-2-sulfonyloxy) imino-2-phenylacetonitrile From a mixture of 1.26 g of 2-hydroxyimino-2-phenylacetonitrile, 2.91 g of 9,10-dimethoxyanthracene-2-sulfonyl chloride, 50 ml of dichloromethane, and 0.87 g of triethylamine was obtained 3.61 g of a yellow solid product by the same procedures as in Example 1. The light irradiation was carried out on this compound in the same way as in Example 1, and the leuco dye of the above formula (VI) was added. The compound became a brilliant blue color, and the generation of an acid was observed.

EXAMPLE 3

Synthesis and Evaluation of N-(9,10-Dimethoxyanthracene-2-sulfonyloxy)phthalimide A mixture of 0.98 g of N-hydroxyphthalimide, 2.02 g of 9,10-dimethoxyanthracene-2-sulfonyl chloride and 40 ml of tetrahydrofuran was stirred on an ice bath, and 0.34 g of triethylamine was added.

The mixture was stirred at room temperature. After confirming that the starting materials were almost dissolved using thin-layer chromatography, the mixture was put in ice water. A precipitated oily product was extracted with ethyl acetate. The extract was dried, and the solvent was distilled off. Acetone was added to the resulting mixture, and filtration was performed to obtain 1.25 g of the desired product as a yellow solid.

Light irradiation was carried out on this compound in the same way as in Example 1, and the leuco dye of the above formula (VI) was added, whereby it became a brilliant blue color and the generating of an acid was observed.

While the invention has been described in detail and with reference to specific embodiments thereof, it will be apparent to one skilled in the art that various changes and modifications can be made therein without departing from the spirit and scope thereof.

What is claimed is:

1. A compound capable of generating an acid by light irridiation, wherein said compound is selected from the group consisting of (i) oxime sulfonic acid esters of formula (I):

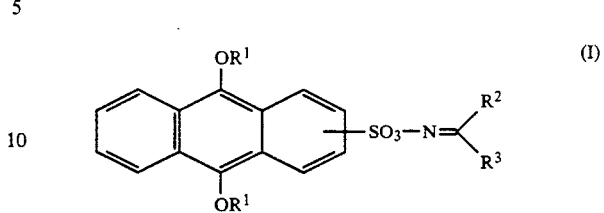

(I)

wherein $R^1$ is a $C_{1-8}$ alkyl group, each or $R^2$ and $R^3$ is selected from the group consisting of a hydrogen atom, a substituted or unsubstituted $C_{1-8}$ alkyl group, a substituted or unsubstituted $C_{6-10}$ carbocyclic aryl group and a cyano group, and $R^2$ and $R^3$ may optionally combine to form a ring having 4 to 14 carbon atoms, and wherein substituents on said alkyl and carbocyclic aryl groups are selected from the group consisting of halogen, $C_{1-6}$ alkyl, $C_{6-10}$ carbocyclic aryl, $C_{1-8}$ alkoxy carbonyl, mono-($C_{1-8}$ alkyl) amino carbonyl, di-($C_{1-8}$ alkyl) amino carbonyl, $C_{1-8}$ alkoxy and nitro; and (ii) N-hydroxyimidesulfonic acid esters of formula (II):

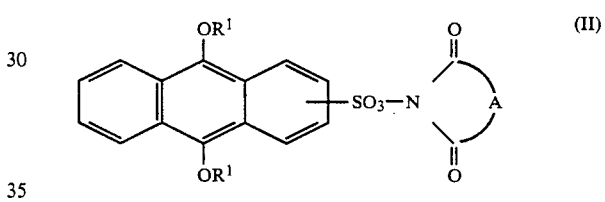

(II)

wherein $R^1$ is a $C_{1-8}$ alkyl group, and A is a group selected from the group consisting of a substituted or unsubstituted $C_{6-10}$ arylene group, a substituted or unsubstituted $C_{2-10}$ alkylene group and a substituted or unsubstituted $C_{2-10}$ alkenylene group, and wherein substituents on said arylene, alkylene and alkenylene groups are selected from the group consisting of halogen, $C_{1-6}$ alkyl, $C_{6-10}$ carbocyclic aryl, $C_{1-8}$ alkoxy carbonyl, mono-($C_{1-8}$ alkyl) amino carbonyl, di-($C_{1-8}$ alkyl) amino carbonyl, $C_{1-8}$ alkoxy and nitro.

2. The compound capable of generating an acid by light irradiation as claimed in claim 1, which is an oxime sulfonic acid ester of formula (I):

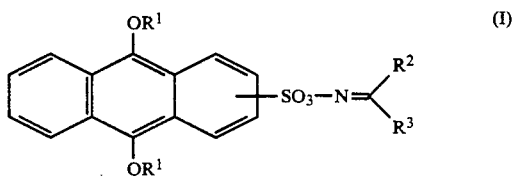

(I)

wherein $R^1$ is a $C_{1-4}$ alkyl group, each of $R^2$ and $R^3$ is selected from the group consisting of a hydrogen atom, a $C_{1-6}$ alkyl group, a halogenated $C_{1-6}$ alkyl group, a $C_{6-10}$ carbocyclic aryl group and a cyano group, and $R^2$ and $R^3$ may optionally combine to form a ring having 4 to 14 carbon atoms.

3. The compound capable of generating an acid by light irradiation as claimed in claim 1, which is an N-hydroxyimidesulfonic acid ester of formula (II):

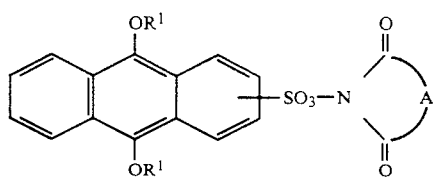 (II)
wherein $R^1$ is a $C_{1-4}$ alkyl group, and A is a group selected from the group consisting of a $C_{6-10}$ arylene group, a $C_{2-6}$ alkylene group, and a $C_{2-6}$ alkenylene group.
* * * * *
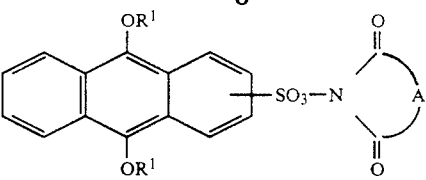 (II)
wherein $R^1$ is a $C_{1-4}$ alkyl group, and A is a group selected from the group consisting of a $C_{6-10}$ arylene group, a $C_{2-6}$ alkylene group, and a $C_{2-6}$ alkenylene group.
* * * * *